(12) United States Patent
Krisch et al.

(10) Patent No.: US 8,178,087 B2
(45) Date of Patent: May 15, 2012

(54) PROCESS OF PRODUCTION OF BACTERIOPHAGE COMPOSITIONS AND METHODS IN PHAGE THERAPY FIELD

(75) Inventors: Henry M. Krisch, Toulouse (FR); Marie-Françoise Prere, Toulouse (FR); Françoise Tetart, Toulouse (FR)

(73) Assignees: Centre National de la Recherche Scientifique —CNRS (FR); Universite Paul Sabatier de Toulouse 3 (FR)

( * ) Notice: Subject to any disclaimer, the term of this patent is extended or adjusted under 35 U.S.C. 154(b) by 309 days.

(21) Appl. No.: 12/295,893

(22) PCT Filed: Apr. 3, 2007

(86) PCT No.: PCT/IB2007/000880
§ 371 (c)(1),
(2), (4) Date: Jan. 15, 2009

(87) PCT Pub. No.: WO2007/113657
PCT Pub. Date: Oct. 11, 2007

(65) Prior Publication Data
US 2009/0232770 A1    Sep. 17, 2009

Related U.S. Application Data

(60) Provisional application No. 60/788,895, filed on Apr. 4, 2006.

(51) Int. Cl.
*A01N 63/00* (2006.01)
*C12N 7/04* (2006.01)
*A61K 31/43* (2006.01)
*A61K 31/00* (2006.01)

(52) U.S. Cl. ............ 424/93.1; 435/236; 514/192; 514/1
(58) Field of Classification Search ................ 424/93.1; 435/236; 514/192, 1
See application file for complete search history.

(56) References Cited

U.S. PATENT DOCUMENTS

| 6,121,036 A | 9/2000 | Ghanbari et al. |
| 6,399,097 B1 | 6/2002 | Fischetti et al. |
| 6,406,692 B1 | 6/2002 | Fischetti et al. |
| 6,423,299 B1 | 7/2002 | Fischetti et al. |

(Continued)

FOREIGN PATENT DOCUMENTS
WO    WO 9739111 A1  *  10/1997
(Continued)

OTHER PUBLICATIONS

Stone, R., "Stalin's Forgotten Cure," *Science*, Oct. 25, 2002, vol. 298, pp. 728-731.

(Continued)

*Primary Examiner* — Rosanne Kosson
(74) *Attorney, Agent, or Firm* — DLA Piper LLP (US)

(57) ABSTRACT

A method for producing bacteriophage stock compositions including (a) incubating a culture medium including at least one bacterial strain, at least one bacteriophage strain that can infect the bacterial strain, and at least one antibiotic, wherein the concentration of the antibiotic in the medium is in a range which causes about 0.1% to about 99.9% inhibition of the growth of the bacterial strain in the absence of the bacteriophage strain; (b) continuing incubation of the culture medium until bacterial lysis occurs, thereby obtaining a bacteriophage lysate; and preparing a crude bacteriophage extract from the culture medium.

15 Claims, 4 Drawing Sheets

U.S. PATENT DOCUMENTS

| | | |
|---|---|---|
| 2001/0026795 A1 | 10/2001 | Merril et al. |
| 2002/0001590 A1 | 1/2002 | Kelly et al. |
| 2002/0044922 A1 | 4/2002 | Mardh |
| 2002/0058027 A1 | 5/2002 | Nelson et al. |

FOREIGN PATENT DOCUMENTS

| | | |
|---|---|---|
| WO | 00/69269 A1 | 11/2000 |
| WO | 01/93904 A1 | 12/2001 |
| WO | 02/07742 A2 | 1/2002 |
| WO | 2004/052274 A2 | 6/2004 |
| WO | 2004/062677 A1 | 7/2004 |
| WO | 2005/009451 A1 | 2/2005 |
| WO | WO 2005046579 A2 * | 5/2005 |

OTHER PUBLICATIONS

Shigenobu Matsuzuki et al., "Bacteriophage therapy: a revitalized therapy against bacterial infectious diseases," Journal of Infection and Chemotherapy, vol. 11, No. 5, Oct. 2005, pp. 211-219 (XP-002443786).

Mikael Skurnik et al., "Phage therapy: Facts and fiction," International Journal of Medical Microbiology, vol. 296, No. 1, Feb. 15, 2006, pp. 5-14 (XP-005250903).

* cited by examiner

| Phages | TIC | CRO | CTX | CFM | AM | PIP | ATM | E | NA |
|---|---|---|---|---|---|---|---|---|---|
| | | | β-lactams | | | | | Macrolide | Quinolone |
| T4 | + | +++ | +++ | +++ | ++ | +++ | +++ | - | ++ |
| T6 | +/- | + | +++ | +++ | +++ | + | ++ | - | + |
| T2 | - | + | +/- | ++ | ++ | - | ++ | - | + |
| AC3 | ++ | +/- | +++ | +++ | + | +++ | +++ | - | +/- |
| K3 | + | ++ | + | +++ | +++ | + | +/- | - | ++ |
| OX2 | +/- | - | ++ | +++ | + | - | +++ | - | + |
| RB5 | ++ | +++ | + | +++ | - | ++ | +++ | - | ++ |
| RB14 | - | +++ | +++ | +++ | + | +++ | ++ | - | +/- |
| RB33 | ++ | +++ | ++ | +/- | +/- | +++ | +++ | - | ++ |
| RB42 | +++ | ++ | +++ | +++ | +++ | +++ | +++ | - | - |
| RB43 | ++ | ++ | +++ | +++ | +++ | +/- | +++ | - | + |
| RB49 | ++ | +/- | +++ | +++ | ++ | +++ | +++ | - | +++ |
| φ1 | + | ++ | +++ | ++ | - | ++ | +++ | - | +++ |
| RB69 | ++ | ++ | +++ | +++ | ++ | +++ | +++ | - | ++ |
| PST | + | +/- | +++ | +++ | - | +++ | + | - | ++ |
| SV76 | ++ | - | +++ | +++ | ++ | +++ | +++ | - | +++ |
| C16 | ++ | ++ | +++ | +++ | +++ | +++ | +++ | - | + |
| M1 | +++ | +++ | +++ | +++ | +++ | +++ | +++ | - | +++ |

Figure 2

PROCESS OF PRODUCTION OF BACTERIOPHAGE COMPOSITIONS AND METHODS IN PHAGE THERAPY FIELD

RELATED APPLICATIONS

This is a §371 of International Application No. PCT/IB2007/000880, with an international filing date of Apr. 3, 2007 (WO 2007/113657 A1, published Oct. 11, 2007), which is based on U.S. Provisional Patent Application No. 60/788,895, filed Apr. 4, 2006.

TECHNICAL FIELD

This disclosure relates to the use of bacteriophages to treat infectious diseases, more particularly, to methods for production of bacteriophage compositions, the methods reducing the production volume and elevating production yield allowing the production of large quantities of bacteriophages more cheaply. The disclosure further relates to methods for treating bacterial infection.

BACKGROUND

Bacteriophages (phages) are the viruses that infect bacteria as distinguished from animal and plant viruses. Phages can have either "lytic" or "lysogenic"life cycle.

Phages multiplying in a lytic cycle cause lysis of the host bacterial cell at the end of their life cycle. Temperate phages have the possibility of an alternative life cycle where they integrate their genomic DNA into the host bacterial chromosome so that this "prophage" is propagated passively by the bacterial chromosome's replication apparatus. Although largely inert and noninfectious prophages can, under some circumstances excise from the host genome, replicate in the lytic mode, produce numerous progeny and finally cause lysis of the host bacterium.

The natural capacity of phages to infect and subsequently efficiently kill bacteria, together with the enormous specificity of the phage-bacterial interactions, is the basic biological phenomena on which phage therapy is founded. Those phages that lack the capability to enter the alternative lysogenic life cycle, the so-called virulent phages, are the most suitable type of phage to employ for therapy.

Phage therapy was first proposed by D'HERELLE (The bacteriophage: its role in immunity; Williams and Wilkens Co; *Waverly Press Baltimore USA,* 1922). Although offering much initial promise as a effective means to treat diseases caused by bacterial infections, its therapeutic value remained controversial. Once antibiotic therapy became the treatment of choice for bacterial infections in the 1940s, little further attention was paid to phage therapy. The ultimate reason for this marked lack of enthusiasm for phage therapy was that no simple and reliable formulation of a efficacious bacteriophage composition emerged, i.e., one that is sufficiently virulent, non-toxic, host-specific, and yet with a wide enough host range to be of practical use. As a consequence research on the therapeutic use of phage stagnated for many years.

The extensive use of antibiotics has led to an increase in the number of bacterial strains resistant to most or all available antibiotics, causing increasingly serious medical problems and raising widespread fears of return to a pre-antibiotic era of untreatable bacterial infections and epidemics.

The ability to easily sequence entire microbial genomes and to determine the molecular basis of their pathogenicity promises novel, innovative approaches for the treatment of infectious diseases, but "traditional" approaches are also being re-explored with increasing emphasis. One such approach is bacteriophage therapy, which is attracting renewed attention as a potential weapon against drug-resistant microbes and hard-to-treat infection (STONE; *Science; vol.* 298; p: 728-731, 2002).

With the development of molecular biology, phage received much attention because they proved to be easy and extremely useful as model systems for fundamental research. Today phages are widely used in numerous molecular biology techniques (e.g., the identification of bacteria strains) and good laboratory procedures are available for the isolation of highly pure phage compositions.

The techniques of molecular biology can now also be applied to the field of phage. therapy. For example, WO 00/69269 discloses the use of a certain phage strain for treating infections caused by Vancomycin-sensitive as well as resistant strains of *Enterococcus faecium*, and WO01/93904 discloses the use of bacteriophage, alone or in combination with other antimicrobial agents, for preventing or treating gastrointestinal diseases associated with bacterial species of the genus *Clostridium*.

US 2001/0026795 describes methods for producing bacteriophage modified to delay their inactivation by the host immune system, and thus increasing the time period in which the phage remain active to kill the bacteria.

US 2002/0001590 discloses the use of phage therapy against multi-drug resistant bacteria, specifically methicillin-resistant *Staphylococcus aureus*, and WO 02/07742 discloses the development of bacteriophage having an exceptionally broad host range.

The use of phage therapy for the treatment of specific bacterial-infectious disease is disclosed, for example, in US 2002/0044922; US 2002/0058027 and WO 01/93904.

However, commercial scale production of bacteriophage compositions and especially for therapeutic use is still a limiting factor. In current techniques, the titer of the phage composition is low, usually in the range of $10^9$-$10^{11}$ pfu/ml on a laboratory scale, and $10^7$-$10^9$ on a commercial scale, whereas the titer typically required for phage therapy is greater than $10^{12}$ pfu/ml.

Additionally, to reach the desirable levels of phage titer, very large volumes of liquid phage infected bacterial cultures are required.

As described herein below, the dosage for phage therapy is in the range of $10^6$ to $10^{13}$ pfu/Kg body weight/day, with $10^{12}$ pfu/Kg body weight/day suggested as a preferable dosage. According to the commonly liquid culture methods for phage production, attaining a phage yield equivalent to single daily dose of bacteriophage for a person would require a production volume of 5-10 liters. Commercial production of phage stock composition of one specific phage type would therefore involve the growth of cultures in a volume range of thousands of liters which even with large-volume fermenters would require multiple runs.

Such a large volume of liquid requires the use of large scale, and very expensive fermenters that are costly to operate and to maintain. Moreover, the subsequent processes of phage purification, at least in part, must also be performed with large volumes of liquid, making working under good manufacturing practice (GMP), necessary for the production of pharmaceutical compositions, very hard to achieve technically and economically.

In fact, a reasonable estimation of the cost for clinical trials in the field of phage therapy would be very high, one the reason being that the benefit of using a "cocktail" of different phages for effective treatment, would require that each phage be prepared separately in the special GMP facilities required for FDA approval. This implies, at least initially, that phage therapy would be relatively expensive.

Therefore, there is a recognized need for, and it would be highly advantageous to have a method for the commercial production of phage compositions that increases the phage yield, reduces manufacturing volume so that proven, economical, small-volume purification processes can be applied to the obtained phage extract.

SUMMARY

We provide methods for producing bacteriophage stock compositions comprising (a) incubating a culture medium comprising at least one bacterial strain, at least one bacteriophage strain that infect the bacterial strain, and at least one antibiotic, wherein the concentration of the antibiotic in the medium is in the range which causes about 0.1% to about 99.9% inhibition of the growth of the bacterial strain in the absence of the bacteriophage strain; (b) continuing the incubation of the culture medium until bacterial lysis occurs, thereby obtaining a bacteriophage lysate; and (c) preparing a crude bacteriophage extract from the culture medium.

We further provide methods for treating a mammal suffering from a bacterial infection comprising the step of administrating to the mammal a composition comprising an effective amount of at least one bacteriophage strain, simultaneously or separately in combination with a composition comprising at least an effective amount of an antibiotic, wherein (a) the effective amount of the antibiotic enables to obtain an antibiotic concentration which is in the range which causes about 0.1% to about 99.9% inhibition of the growth of the bacterial strain in the absence of the bacteriophage strain, preferably about 0.1% to about 99.9% inhibition of the in vitro growth of the bacterial strain in the absence of the bacteriophage; and (b) the bacteriophage strain is virulent for at least one of the bacterial strain responsible of the bacterial infection.

BRIEF DESCRIPTION OF THE DRAWINGS

FIG. 2 shows the synergy between myoviridae bacteriophages—i.e., "T4-like" bacteriophage genus—production and *E. coli* AS19 growth in the presence of low doses of antibiotic of the quinolone, β-lactam and macrolide types. TIC: Ticarcillin; CRO: Ceftriaxone; CTX: Cefotaxime; CFM: Cefixime; AM: Ampicillin; PIP: Piperacillin; ATM: Azetreonam; E: Erythrocine; NA: Nalidixic acid. (−): no synergy; (+/−): barely detectable synergy; (+): little synergy; (++): good synergy; (+++): strong synergy.

DETAILED DESCRIPTION

Figure 1:
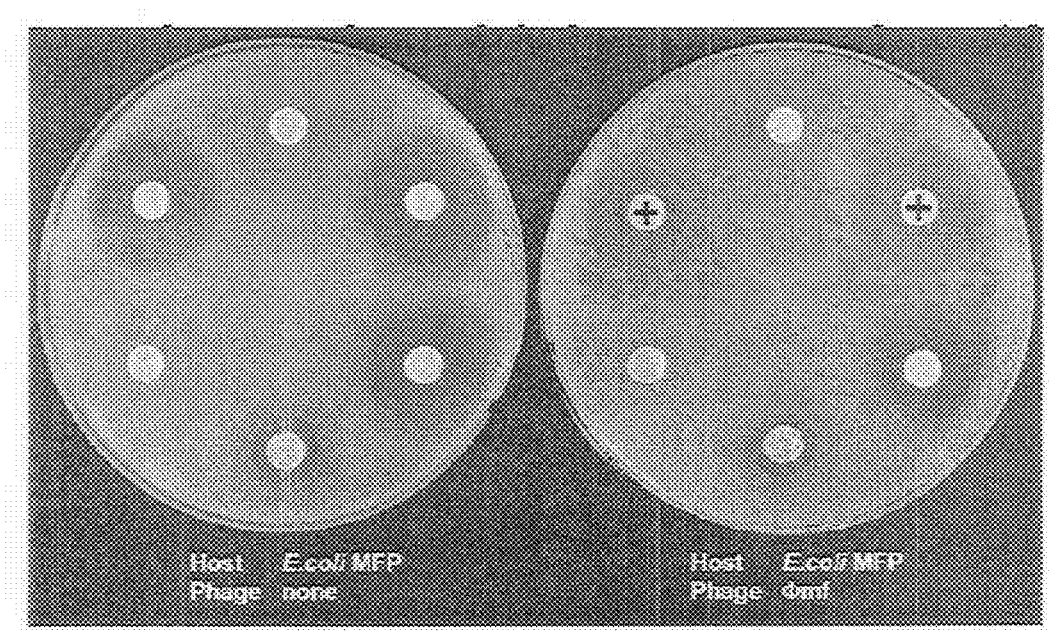
FIG. 1 shows the effect on phage growth and bacterial growth of various types of antibiotics. Only the antibiotic disks (ATM & CFM) marked with a "+" gave a good stimulation of phage φMFP growth.

Our methods relate to the field of phage (bacteriophage), and more especially to the field of phage therapy. Phage therapy, which was an active area of medical research and clinical trials in Eastern Europe during the middle of the twentieth century, has gained renewed attention in the West since the last decade.

There are several basic reasons why the concept of bacteriophage therapy for human or veterinary use has not been reduced successfully to practice: (i) the efficacy of phage therapy was shown to be marginal or even negligible; (ii) unacceptable toxic side effects have been observed, mainly due to the use of bacteriophage compositions contaminated with bacterial debris typically containing toxins; (iii) better alternatives, such as conventional chemical antibiotics, were developed; (iv) appearance of phage-resistant bacterial strains due to the selection of bacterial mutants with altered phage receptors on their surface which allows them to resist phage infection; and (vi) rapid removal of the bacteriophage from the body once the composition was injected or ingested, before the phage could attain their targets, pathogenic bacteria. Extensive research in the field of phage molecular biology has advanced practical knowledge on bacterial-phage interactions and revealed new techniques that may be utilized to overcome at least some of the above described problems that had previously prevented the development of phage therapy as a reliably effective therapeutic tool.

In this context, we provide methods for large-scale production of bacteriophage, in which each step is easy to perform, does not require large volumes, and is therefore more appropriate for a process that requires stringent validation procedures.

In the case of production of pharmaceutical compositions comprising phages for use in phage therapy, this process includes several basic steps corresponding to (i) phage typing to establish susceptibility of the pathogenic bacteria; (ii) selecting the correct phage or phage panel; (iii) picking a single plaque for each phage type to ensure uniform preparation; (iv) obtaining a high phage titer; (v) collecting the phage; (vi) removing host bacteria from the phage crude extract; (vii) purifying the bacteriophage crude extract from endotoxins and other bacterial debris.

A major hindrance to the development of phage therapy has been the limitations of the technologies employed in the preparation of the phages that result in endotoxin-contaminated pharmaceutical compositions that are also not sufficiently biologically active. The reduced production volume achieved using our methods overcomes problems previously encountered with the technologies used to obtain bacteriophage stock compositions.

Our methods for preparing bacteriophages to obtain bacteriophage stock compositions comprise the steps of (a) incubating a culture medium comprising at least one bacterial strain, at least one bacteriophage strain that infect the bacterial strain, and at least one antibiotic, wherein the concentration of the antibiotic in the medium is comprised in the range, which causes about 0.1% to about 99.9% inhibition of the growth of the bacterial strain in the absence of the bacteriophage; (b) continuing incubation of the culture medium until bacterial lysis occurs, thereby obtaining a bacteriophage lysate; and (c) preparing a crude bacteriophage extract from the culture medium.

Preferably, the concentration of the antibiotic severely inhibits cell division, but permits cell elongation to continue normally so that very long filamentous cells are formed. At this concentration, there is little increase in cell number, but no significant loss of cell viability.

The concentration of the antibiotic in the medium may be in the range which causes about 1% to about 99% inhibition of the growth of the bacterial strain in the absence of the bacteriophage, preferably about 10% to about 90% inhibition, as an example about 20% to about 80% inhibition or 40% to about 60%, and most preferably about 50% (IC50) inhibition of the growth of the bacterial strain in the absence of the bacteriophage.

Methods for determining the optimally effective concentrations of antibiotics are known. As an example, the methods can comprise incubation of a defined bacterial strain in different growth liquid mediums (e.g., LB) with or without a defined antibiotic with a large range of concentrations. The analysis of the growth kinetic of the bacterial strain in the liquid mediums with different concentrations of the antibiotic (e.g., determination the OD at 600 nm and CFU/ml of the cultures at different times of incubation) enables to establish the relation between a given concentration of the antibiotic and the percentage of bacterial strain growth inhibition resulting of the concentration in the medium.

Methods for producing bacteriophages are known and involve two alternate techniques, corresponding to a culture in a liquid medium or in a semi-solid medium.

Liquid and semi-solid mediums are known.

Preferably, our methods comprise growing the bacterial strain infected by the bacteriophage strain in a liquid medium. Such liquid mediums are known, and examples of such mediums are described in Mark H. ADAMS (Bacteriophages, Interscience Publishers, New York, 1959).

Alternatively, seed cultures for inoculation are cultured in semi-solid agar on a plate of solid agar.

The methods can further comprise other steps for improving the quality of the bacteriophage stock composition or facilitate the production procedure, including, but not limited to, steps of periodic tittering, purification, automation, formulation and the like.

Purification of the bacteriophages can be obtained by known methods. As an example, the culture medium can be filtered through a very small pore size filter to retain the targeted contaminant—i.e., the bacteria—, and permit the smaller bacteriophage to pass through. Typically, a filter having a pore size in the range of from about 0.01 to about 1 µm can be used, preferably from about 0.1 to about 0.5 µm, and more preferably from about 0.2 to about 0.4 µm. The culture medium can be also purified from bacterial debris and endotoxins by dialysis using the largest pore membrane that retains bacteriophages, where the membrane preferably has a molecular cut-off of approximately $10^4$ to about $10^7$ daltons, preferably within the range of from about $10^5$ to about $10^6$ daltons. Many other suitable methods can be performed as disclosed for example in US 2001/0026795; US 2002/0001590; U.S. Pat. Nos. 6,121,036; 6,399,097; 6,406,692; 6,423,299; and WO 02/07742, among others.

The antibiotic may be selected from quinolones and β-lactams families, preferably in the β-lactams family.

Quinolones family and derivatives thereof are known. Examples of such compounds include Cinoxacin, Ciprofloxacin, Enoxacin, Fleroxacin, Flosequinan, Flumequine, Pomefloxacin, Nalidixic acid, Norfloxacin, Ofloxacin, Oxolinic acid, Pefloxacin, Pipemidic acid, Piromidic acid, Rosoxacin, and Sparfloxacin.

β-lactams family is also known. Examples of such compounds include Amidinocillin, Amoxicillin, Ampicillin, Apalcillin, Aspoxicillin, Azidocillin, Azlocillin, Aztreonam, Bacampicillin, Benzylpenicillic acid, Carbenicillin, Carfecillin, Carindacillin, Carumonam, Cefaclor, Cefadroxil, Cefamandole, Cefatrizine, Cefazedone, Cefazolin, Cefbuperazone, Cefixime, Cefmenoxime, Cefotaxime, Ceftizoxime, Cefmetazole, Cefminox, Cefodizime, Cefonicid, Cefoperzone, Ceforanide, Cefotetan, Cefotiam, Cefoxitine, Cefpimizole, Cefpiramide, Cefpodoxime proxetil, Cefroxadine, Cefsulodin, Ceftazidime, Cefteram, Ceftezole, Ceftibuten, Ceftiofur, Ceftizoxime, Ceftriaxone, Cefuroxime, Cefuzonam, Cephacetrile, Cephalexin, Cephaloglycin, Cephaloridine, Cephalosporin C, Cephalothin, Cephapirin, Cepharanthine, Cephradine, Clometocillin, Cloxacillin, Cyclacillin, Dicloxacillin, Diphenenicillin, Epicillin, Fenbenicillin, Flomoxef, Floxacillin, Hetacillin, Imipenem, Lenampicillin, Metampicillin, Methicillin, Mezlocillin, Moxolactam, Nafcillin, Oxacillin, Penamecillin, Penamethate hydriodide, Penicillin, Penimepicycline, Phenethicillin, Piperacillin, Pivampicillin, Pivcefalexin, Propicillin, Quinacillin, Sulbenicillin, Sulfazecin, Talampicillin, Temocillin, Ticarcillin, and Tigemonam.

The bacterial strain may be *staphylococci, yersinia, hemophili, helicobacter, mycobacterium, streptococci, neisseria, klebsiella, enterobacter, proteus, bacteroides, pseudomonas, borrelia, citrobacter, escherichia, salmonella, propionibacterium, treponema, shigella, enterococci* and *leptospirex.*

Such bacterial strains are known and comprise *Staphylococcus aureus, Staphylococcus epidermidis, Helicobacter pylori, Streptococcus pneumoniae, Streptococcus mutans, Streptococcus oralis, Streptococcus parasanguis, Streptococcus pyogenes, Streptococcus viridans,* Group A *Streptococcus* and *anaerobic streptococcus, Hemophilus influenzae, Shigella dysenteriae, Mycobacterium tuberculosis, Mycobacterium leprae, Mycobacterium asiaticum, Mycobacterium intracellulare, Mycoplasma pneumoniae, Mycoplasma hominis, Neisseria meningitidis, Neisseria gonorrhoeae, Klebsiella pneumoniae, Pseudomonas aeruginosa, Propionibacterium acnes, Treponema pallidum, Treponema pertanue, Treponema carateum, Escherichia coli, Salmonella typhimurium, Borrelia burgdorferi, Yersinia pestis, Leptospira,* such as *Leptospirea icteohaemorrhagiae, Citrobacter freundii.*

We use any bacteriophage, preferably bacteriophages that are virulent for the bacterial strain used in the method. As an example, bacteriophage extract can be derived from microorganisms using. known methods. (See, American Type Culture Collection Catalogue of Bacteria and Bacteriophage, $18^{th}$ Edition, page 402-411, 1,992). Such samples can be collected as an example from individuals who suffer from a bacterial infection. Various samples can be taken from various places on the body including the throat, blood, urine, feces, spinal fluid, nasal mucosa, skin, washings from the larynx and trachea, and the like.

Sample sites can be selected depending upon the target organism. For example, a throat swab likely would be used to collect a sample of a given *streptococcus* strain, a skin culture likely would be used to collect a sample of a given strain of *staphylococcus*, a spinal fluid or blood sample likely be used to collect a sample of *Neisseria meningitidis*, a urine sample can be used to collect samples of *Escherichia coli*, and the like.

Those skilled in the art are capable of obtaining an appropriate sample from the respective locus, given the target organism. Alternatively, bacterial strains can be obtained from various laboratories including those available from the National Institutes for Health (NIH), the ATCC and the like.

The specific bacteria-bacteriophage combination can then be further selected according to the intended use. For example, if the desired use is to provide prophylaxis or therapy for staphylococcal infections, one or more strains of staphylococcal bacteria are used as the bacterial host organisms. In this same example, one or more bacteriophages that are specific for staphylococcal bacteria, or are at least capable of having a productive infection in staphylococcal bacteria, are used to create the therapeutic staphylococcal lysate.

The bacteriophage strain may be selected from Cystoviridae, Leviviridae, Myoviridae, Podoviridae, Siphoviridae, Corticoviridae Inoviridae, Microviridae, and Tectiviridae families, preferably from Myoviridae, Podoviridae and Siphoviridae families, and most preferably in the Myoviridae family.

The Cystoviridae family corresponds to RNA phages and contains one genus (Cystovirus) with one member bacteriophage phi 6.

The Leviviridae family corresponds also to RNA bacteriophages having a linear, positive-sense single-stranded RNA genome, and infecting enterobacteria, caulobacter, and pseudomonas. This family comprises allolevivirus and levivirus genus having no separate gene for cell lysis and a separate gene for cell lysis respectively.

The three Myoviridae, Podoviridae, and Siphoviridae families correspond to the Caudovirales' order.

The Myoviridae family comprises bacteriophages, which are characterized by complex contractile tails and includes, as examples, bacteriophage mu, P1, P2, and T4. Most preferably, the myoviridae comprises bacteriophages of the "T4-like" genus.

The Podoviridae family comprises bacteriophages, which are characterized by short, non-contractile tails, and includes, as examples, bacteriophages N4, P22, T3, and T7.

The Siphoviridae family comprises bacteriophages, which are characterized by long, non-contractile tails, and includes, as examples, bacteriophages hk022, lambda, T5, BF 23.

The Corticoviridae family comprises icosahedral, lipid-containing, non-enveloped bacteriophages, and contains one genus (Corticovirus), which includes bacteriophage PM2.

The Inoviridae family comprises rod-shaped or filamentous bacteriophages consisting of single-stranded DNA. This family has two genera: inovirus and plectrovirus. The inovirus genus comprises bacteriophages that infect enterobacteria, pseudomonas; vibrio; and xanthomonas, and includes, as examples, bacteriophages ike, m13 and pf1. The plectrovirus genus comprises bacteriophages that infect Acholeplasma and Spiroplasma.

The Microviridae family comprises lytic bacteriophages infecting enterobacteria; spiroplasma; bdellovibrio, and chlamidia. It contains four genera: microvirus, spiromicrovirus; bdellomicrovirus; and chlamydiamnicrovirus. The microvirus genus comprises isometric single-stranded DNA bacteriophage, and includes, as examples, bacteriophages G4 and phi x 174.

The Tectiviridae family comprises lipid-containing bacteriophages with double capsids, which infect both gram-negative and gram-positive bacteria. This family has one genus, and includes, as examples, bacteriophage prd1.

We further provide methods for treating a mammal, preferably a human suffering from a bacterial infection comprising the step of administrating to the mammal a composition comprising an effective amount of at least one bacteriophage, simultaneously or separately in combination with a composition comprising at least an effective amount of an antibiotic, wherein (a) the effective amount of the antibiotic enables to obtain an antibiotic concentration which is in the range which causes about 0.1% to about 99.9% inhibition of the growth of the bacterial strain in the absence of the bacteriophage; and (b) the bacteriophage strain is virulent for at least one of the bacterial strain responsible of the bacterial infection.

The effective amount of the antibiotic may enable obtaining a concentration in the range which causes about 1% to about 99% inhibition of the growth of the bacterial strain in the absence of the bacteriophage, preferably about 10% to about 90% inhibition, as an example about 20% to about 80% inhibition or about 40% to about 80% inhibition, and most preferably about 50% (IC50) inhibition of the growth of the bacterial strain in the absence of the bacteriophage.

The antibiotic may be selected from quinolone and β-lactam families, preferably in the β-lactam family.

We also may use any bacteriophage, preferably bacteriophages that are virulent for at least one of the bacterial strains responsible of the bacterial infection. Such bacteriophage can be selected as described previously.

Determining an effective amount of the bacteriophage to be administrated entails standard evaluations. An assessment in this regard would generate data concerning the phage's bioavailability, absorption, degradation, serum and tissue levels and excretion, as well as microorganism levels, markers, and cultures. The appropriate dosage and duration of treatment can be ascertained by those skilled in the art using known techniques. As an example, an effective amount of bacteriophage is in the range of $10^6$ to $10^{13}$ pfu/Kg body Weight/day.

The bacteriophage and antibiotic compositions can be administrated intravenously, intranasally, orally, or other known routes of administration of medicaments, for a period of time required for effectively treating the bacterial infection. The expression "treating a bacterial infection," as it is used throughout this description denotes killing or obliterating sufficient bacteria to render these microorganisms ineffective in causing an infection of the host organism.

Thus, the compositions can comprise a pharmaceutically acceptable carrier. As an example, an injectable bacteriophage composition may contain about 10 mg of human bovin serum albumin and from about 20 to 200 μg of bacteriophage per milliliter of phosphate buffer containing NaCl. Other pharmaceutically acceptable carriers include aqueous solutions, non-toxic excipients, including salts, preservatives, buffers and the like, as described in Remington's Pharmaceutical Sciences ($15^{th}$ Ed. Easton: Mack Publishing Co, p: 1405-1412 and 1461-1487, 1975).

Bacteriophage's and antibiotic's compositions may be administrated simultaneously, preferably the administrated composition comprised simultaneously at least one bacteriophage and at least one antibiotic in effective amounts.

The composition comprising at least a bacteriophage may be administrated to a mammal within the period ranging from about one day before or after the administration of a composition comprising at least one antibiotic, preferably from about 12 hours before or after, as an example from about 6 hours before or after, and more preferably from about 1 hour before or after the administration of a composition comprising at least one antibiotic.

Our methods will be understood more clearly on reading the description of the experimental studies performed in the context of representative examples, which should not be interpreted as being limiting in nature.

EXAMPLES

1) Identification of Abnormal Bacterial Lysis Plaques Produced by Phage Growing in the Presence of Antibiotics To test the antibiotic sensitivity of bacteria isolated from children hospitalized with severe urinary tract infections and to save time, a nutrient Petri plate was directly inoculated with a dilution of child's urine and a series of antibiotic sensitivity test disks were placed on the surface of the agar.

As expected, the results have shown that the urine was contaminated with an uropathogenic *Escherichia coli* strain. Nevertheless, and unexpectedly, the results have also shown the appearance of phage plaques around antibiotic sensitivity test disks, and thus that strain was infected by bacteriophages. Remarkably, the size of these phage plaques were much larger in the zone of non lethal concentrations of antibiotic that encircled β-lactam antibiotic disks (e.g. ATM (aztreonam) and CFM (cefixime)) but not the other drugs (Tetracycline, Trimethoprim and Gentamicin).

Thus, it seems that low dosage of β-lactams somehow stimulated phage growth in this host-phage system.

2) Synergy of β-Lactam Antibiotics (ATM and CFM) and the φmF Bacteriophage when Grown on MFP Bacterial Strain To confirm this appearance of larger phage plaques, a single colony of the non-infected uropathogenic E. coli (MFP) and a plaque of the contaminating phage (φmF) have been isolated from the original urine sample as described Mark H. ADAMS (Bacteriophages, 1959 Interscience Publishers, New York.

The electron microscopy of the φmF has revealed a typical siphovirus morphology, a long flexible non contractile tail structure, and an isometric icosahedral head of about 60 nm. The DNA sequencing of 25 random segments of the φmF genome has indicated that this bacteriophage is related to the Salmonella typhimurium bacteriophage MB78. The growth of φmF bacteriophage has been tested on different laboratory bacterial strains from the genus E. coli (AS19, CR63, P400, B897, 834a, B40, S/6, $B^E$). These tests have not shown any growth of the φmF bacteriophage on any of these bacterial strains.

A culture of non-infected MFP strain has been grown overnight in LB liquid medium, and then a dilution of the culture either alone or mixed with φmF phage have been inoculated on a series of nutrient Petri plate where different antibiotic sensitivity test disks were placed on the surface.

The results show the resistance of the MFP bacterial strain to some antibiotics including the Amoxicillin β-lactam antibiotic. In these strains, no zone of growth inhibition was observed in the bacteria growing around the disks comprising the antibiotics (see FIG. 1, non-infected E. coli MFP). More importantly, the results demonstrate the sensitivity of the MFP strain to antibiotics including the β-lactam ATM and CFM, and also the non-β-lactam Tetracycline.

Furthermore, the results confirm the synergistic antibiotic effect. The entire surface of the Petri plate was inoculated with a mixture of both the MFP bacterial host and with the phage φmF that could infect it (see FIG. 1, φmF-infected E. coli MFP). As observed previously, the φmF plaques have a significantly larger size only in the zone of non lethal antibiotic concentration around β-lactam ATM and CFM disks (see FIG. 1, disks with cross), for which the MFP bacterial strain is sensitive.

In conclusion, the results show that a synergy occurs between the β-lactams antibiotics and φmF bacteriophage multiplication in the zone where the concentration of the antibiotics is not completely inhibitory for the growth of bacterial strain MFP.

3) Generality of the Synergy between β-Lactam Antibiotics (ATM and CTX) and Bacteriophage Growth on the MFP Bacterial Strain To examine the antibiotic-phage growth synergy with different bacteriophage strains, the MFP bacterial strain has been tested for this effect with a large set of phylogenetically diverse T4 type phages.

Of the >80 T4-type bacteriophage strains tested on the MFP bacterial strain, nine of these were identified in spot tests as able to infect and lyse the MFP strain. These bacteriophages were as follows: RB6, RB8, RB9, RBl5, AC3, RB32, RB33, and T6.

A culture of the MFP bacterial strain was grown overnight in LB liquid medium and a plating culture was prepared. This plating culture was mixed in soft agar with appropriate dilutions of either phage φmF or the nine previously enumerated T4-type bacteriophages and then poured on the surface of a nutrient Petri plate. Subsequently, an antibiotic disk containing either CTX or ATM was placed on the top layer of the nutrient Petri plate.

The results are summarized in the following table:

| Bacteriophage strain | Appearance of larger phage plaques | |
|---|---|---|
| | CTX | ATM |
| RB6 | − | NT |
| RB8 | − | NT |
| RB9 | − | NT |
| RB14 | − | NT |
| RB15 | ++ | ++ |
| AC3 | − | NT |
| RB32 | ++ | ++ |
| RB33 | ++ | ++ |
| T6 | − | NT |
| φmF | +++ | +++ |

NT = Not Tested

These results reveal a synergy between these β-lactams antibiotics and phage multiplication within a zone where the antibiotics mediates a partial growth inhibition of the MFP bacterial host. This synergistic effect is not limited exclusively to the φmF phage strain, and is manifested by other bacteriophage strains totally unrelated to φmF bacteriophage.

4) The Synergy between Bacteriophages and β-Lactam Antibiotics in Host Bacteria Other than the Original MFP Strain where the First Observation of the Synergistic Effect was Made To test the synergy with other bacterial strains, the size of phage plaques have been examined in different bacterial host strains infected with the same bacteriophage, T4, in the presence of either ATM or CTX.

Overnight cultures of the Escherichia. coli bacterial strains AS19, P400, S/6, BE, C600 and MC1061 were inoculated into LB liquid medium grown to exponential phase and a plating culture was prepared. Each bacterial indicator strain was mixed with a dilution of T4 in soft agar and then poured on nutrient Petri plate and a CTX antibiotic test disk was subsequently placed on the surface of the plate.

The results are summarized in the following table:

| Bacterial strain | CTX (Cefotaxime) |
|---|---|
| AS19 | +++ |
| P400 | + |
| S/6 | ++ |
| BE | +++ |
| C600 | + |
| MC1061 | + |

The results show that the synergy between the β-lactams antibiotic growth inhibition and T4 phage multiplication occurs within the zone where there is a non-inhibitory concentration of the antibiotic. This effect is not limited to the MFP Escherichia. coli and occurs with several standard Laboratory strains of E. coli that were tested. In a related experiments, the growth of some T4-type Yersinia phages (PST, RB6, RB32, RB33, MI) were shown to manifest a similar growth synergy with CTX on the bacterial host *Yersinia pseudotuberculosis*. Thus, this synergistic effect the antibiotic is not limited to phages propagating on the *E. coli* host bacteria.

5) The Synergy between Bacteriophages and β-Lactam Antibiotic in *E. coli* AS19 Infected with Diverse T4-Type Phages To further examine the extent and generality of the synergy between bacteriophage and β-lactam antibiotics, we have tested with a series of different T4-type phage strains for their manifestation of this effect. The bacterial host chosen for this and most of the subsequent studies was *E. coli* AS19 an antibiotic permeability mutant. This strain generally gave the most substantial synergistic effect with a wide variety of T4-type phage.

An overnight culture of the AS19 bacterial strain was inoculated into LB liquid medium, grown to exponential phase and a plating culture was prepared. The indicator strain was mixed with a dilution of the various T4-type phages in soft agar and then poured on nutrient Petri plate and a CTX antibiotic test disk was subsequently placed on the surface. The following T4-type bacteriophages strains were tested: RB9, RB32, RB33, RB42, RB49, RB69, C16, SV76, T6, and ϕ-1.

These results are summarized in the following table:

| Bacteriophage strain | Appearance of larger phage plaques with CTX (Cefotaxime) |
|---|---|
| RB9 | +/-- |
| RB32 | +++ |
| RB33 | +++ |
| RB42 | - |
| RB49 | +++ |
| RB69 | - |
| C16 | +++ |
| SV76 | +/- |
| T6 | +/- |
| ϕ-1 | +++ |

The results reveals this β-lactams antibiotic exerts a synergistic effect on the production of diverse T4-type phage at a level of antibiotic that only partially inhibits the *E. coli* AS19 bacteria's growth. Thus, the synergistic antibiotic effect on phage growth extends considerably beyond the original MFP bacterial host and ϕMFP phage system where it was initially observed.

6) The Synergy between Bacteriophages Production and Bacterial Host Growth in the Presence of Low Doses of Antibiotic is not Limited Exclusively to β-Lactam Antibiotics To investigate if this synergy also is also mediated by other antibiotics, the AS19 bacterial strain has been tested with both a series of phylogenetically diverse T-type phages, and a diverse set of different classes of antibiotics.

Again an overnight culture of the AS19 bacterial strain was inoculated into LB liquid medium, grown to exponential phase and a plating culture was prepared. The indicator strain was mixed with a dilution of the various T4-type phages in soft agar and then poured on nutrient Petri plate and a series of different antibiotic test disk was subsequently placed on the surface. The following twelve T4-type bacteriophages strains were tested: T4, T2, T6, OX2, K3, RB33, RB5, RB14, RB49, PHI, 697, and 699.

The results demonstrate that at least one additional class of antibiotics, in addition to the β-lactams, stimulate progeny production by bacteriophages T4 (FIG. 2). This effect only occurs in a narrow range of concentration around the antibiotic disk that is apparently sublethal to the AS19 bacteria, because some stunted bacterial growth still occurs in this zone. In addition to the diverse β-Lactams, at least one quinolone (Nalidix Acid) causes a synergistic effect on phage T4 growth. The unifying characteristic of the all the antibiotics that are synergistically effective is that they mediate, either directly or indirectly, an inhibition of bacterial cell division even in the low dosage range we employed.

Furthermore, T4-like phages have been also tested with a number of other classes of antibiotics than those previously described, and failed to stimulate T4 phage production. These other antibiotics were aminoglycosides (Gentamicin and Amikacin), amphenicols (Choramphenicol), tetracyclines (Tetracycline), 2,4-Diaminopyrimidines (Trimethoprim), sulfonamides (Sulfamethoxazole in combination with Trimethoprim), nitrofuranes (Nitrofurantoin), ansamycins (Rifampin), phosphonic acids (Fosfomycin), and polypeptides (Colistin).

7) Increased Phage Multiplication Associated with the Antibiotic Synergy

To quantitatively determine the augmentation phage multiplication in the infected bacterial strain in the presence or absence of antibiotic.

Different cultures of AS19 bacterial strain infected with three T-type bacteriophage strains—i.e., T4, RB33, and RB49—and where then incubated for 90 minutes in LB liquid medium either with or without CTX (0.003 or 0.03 μg/ml), and then the infected culture was lysed with chloroform and phage titer was determined as described in ADAMS (Bacteriophages, Interscience Publishers, New York, 1959).

The results are summarized in the following table:

| T4-type phage | Titer with no antibiotic (pfu/ml) | Titer with 0.003 μg/ml CTX (pfu/ml) | Titer with 0.03 μg/ml CTX (pfu/ml) |
|---|---|---|---|
| T4 | $1.4 \times 10^{12}$ | $1.3 \times 10^{13}$ | $1.7 \times 10^{13}$ |
| RB33 | $5.4 \times 10^{11}$ | $1.3 \times 10^{12}$ | $6.4 \times 10^{12}$ |
| RB49 | $1.4 \times 10^{11}$ | $1.4 \times 10^{11}$ | $7 \times 10^{11}$ |

The results show that even very low dosage of the antibiotic, and more precisely the β-lactam antibiotic (CTX) mediates a significant increase in T4-type phage production with more than 10 fold for T4 and RB33, and nearly 5 fold for RB49.

8) Mechanism Associated with the Observed Synergy

Figure 3:
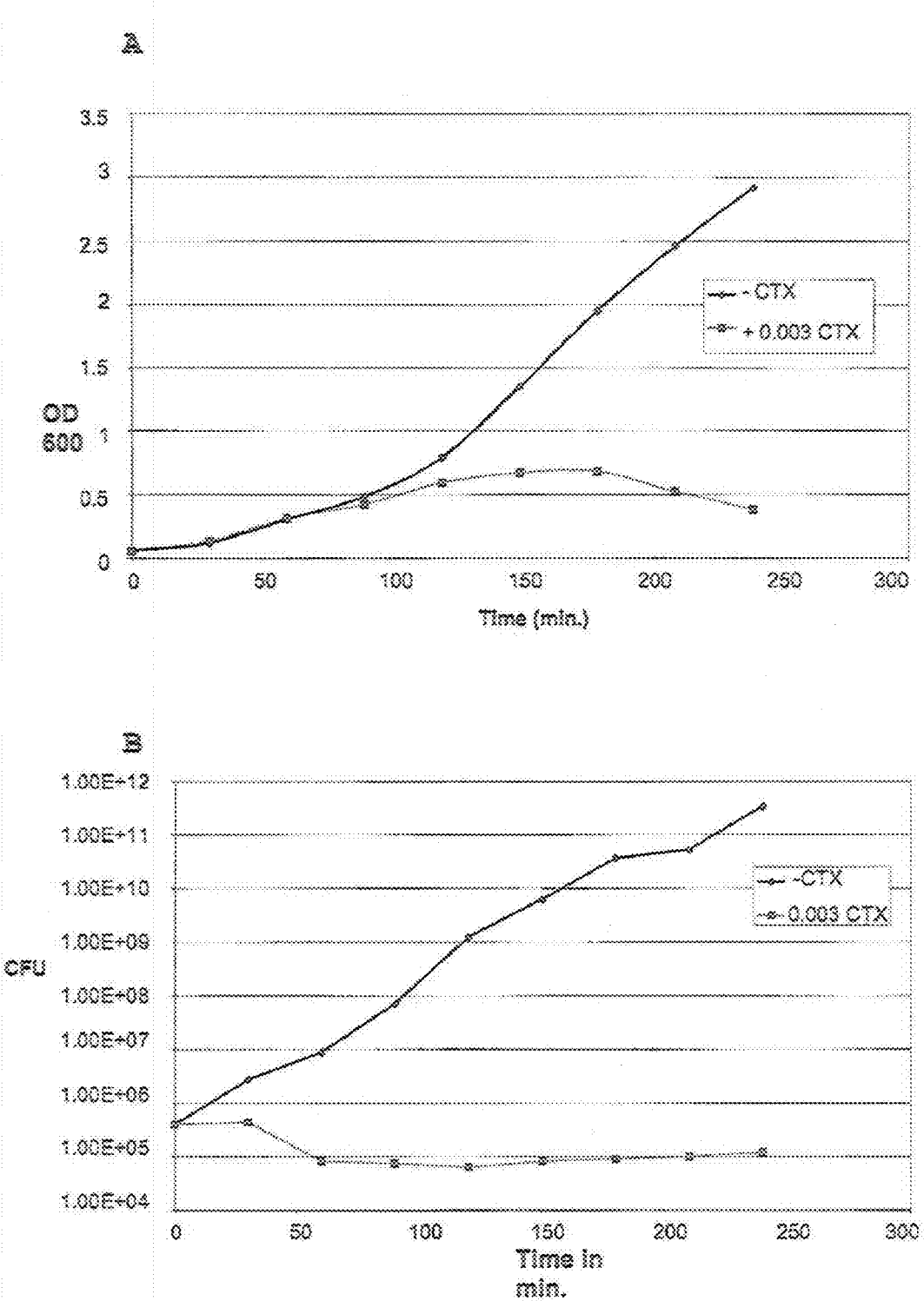
FIG. 3 shows the *E. coli* AS19 strain grown either with (0.003 CTX) or without (−CTX) 0.003 µg Cefotaxime. Growth was measured either by OD600 (A) or CFU/ml (B). The times (T) is indicated in minutes after addition of CTX to the growth medium.

To examine the effect of low doses of the β-lactam antibiotic CTX on a culture of the AS19 bacterial strain, this bacterial strain was grown in LB liquid medium with CTX at a dosage level (0.003 μg/ml) that produces a substantial effect synergistic when infected with T4 phage. When compared to the control culture without CTX treatment, it is clear that even at this low level of the drug cell division is inhibited although cell viability as assayed by colony forming units is little effected (FIGS. 3A and 3B). Since the optical density of the culture treated with the drug continues to increase for at least two hours after the addition of the drug, it seems likely that the non-dividing cells continue to grow in volume and produce long filamentous cells rather than dividing as they would normally do in the absence of the drug.

To verify that the plausible mechanism for the synergy between the β-lactam antibiotic and augmentation of T4 phage production involved the drug mediated block in cell division, a culture of the AS19 bacterial strain was grown in a LB liquid medium and then infected with T4 phage either with CTX (0.003 μg/ml) or without it. The morphology of the bacteria in culture has been observed by optical microscopy at different times after infection.

Figure 4:
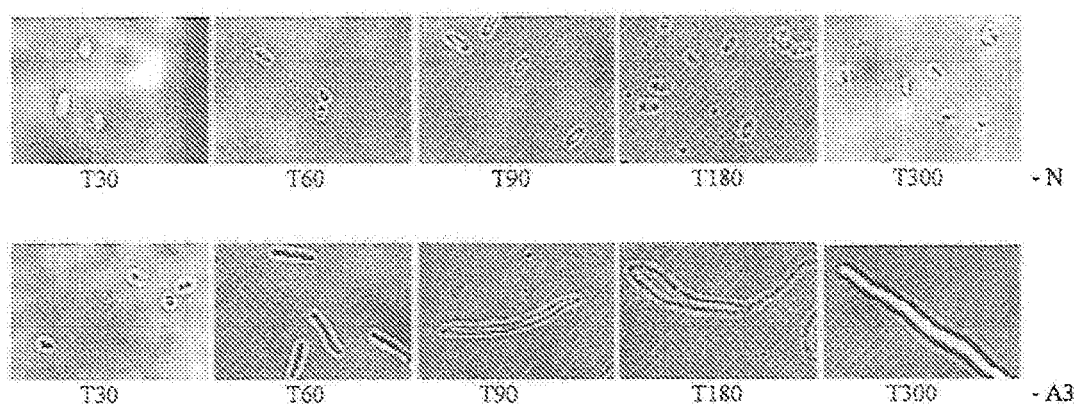
FIG. 4 shows the size of uninfected *E. coli* AS19 cell grown without (N) and with (A3) 0.003 µg Cefotaxime (CTX). The times (T) are indicated in minutes after addition of CTX to the growth medium.

The results show no modification of the bacterial morphology at during the course of infection in the medium without CTX (See FIG. 4, N), whereas in a liquid medium with CTX the cell size of the T4 infected bacteria increases in volume considerably producing long fat filaments by several hours after infection (See FIG. 4, A3).

In conclusion, the synergy between increased phage production an low levels of the antibiotics, and especially β-lactam and quinolone antibiotics, could be direct consequence of an increase in the capacity of the much larger drug treated cells to produce the phage. Presently, we have established similar synergies with bacteria other than *E. coli*—i.e., Yersinia—, and with bacteriophages other than Myoviridae—i.e., Siphoviridae—. More investigation is required to understand the exact details of how a drug mediated block in the host cell's division program leads to a significant augmentation of the phage-infected cells capacity to produce progeny phage. We hypothesize that there has been a evolutionary selection for phages that can more efficiently cannibalize host cells that are unable to further divide and thus propagate in their current environment. If this is true then it may be that in some cases the optimal conditions for phage multiplication may not be exponential cell growth as is widely believed, but rather a terminal burst of phage production in a stressed cell population that would soon die anyway.

We claim:

1. A method for treating a mammal suffering from a bacterial infection comprising,
   (i) administering to said mammal a composition comprising an effective amount of at least one self-replicating bacteriophage strain, simultaneously or separately in combination with a composition comprising at least an effective amount of an antibiotic, wherein (a) said effective amount of said antibiotic is an antibiotic concentration in a range which is non-lethal to the bacterium that causes the infection and causes 0.1% to 99.9% inhibition of bacterial cell division; and (b) said bacteriophage strain is virulent for at least one of the bacterial strains responsible for said bacterial infection, and wherein said antibiotic is at least one selected from the group consisting of Ticarcillin, Ceftriaxone, Cefotaxime, Cefixime, Ampicillin, Piperacillin, Aztreonam, and Nalidixic acid, and the bacteriophage is selected from the group consisting of T4, T6, T2, AC3, K3, OX2, RB5, RB14, RB33, RB42, RB43, RB49, 1, RB69, PST, SV76, C16, and M1.

2. The method according to claim 1, wherein the effective amount of said antibiotic is a concentration in the range which is non-lethal to the bacterium that causes the infection and causes 1% to 99% inhibition of the cell division of said bacterium.

3. The method according to claim 1, wherein the effective amount of said antibiotic is a concentration in the range which is non-lethal to the bacterium that causes the infection and causes 10% to 90% inhibition of the cell division of said bacterium.

4. The method according to claim 1, wherein the effective amount of said antibiotic is a concentration in the range which is non-lethal to the bacterium that causes the infection and causes 20% to 80% inhibition of the growth of said bacterium.

5. The method according to claim 1, wherein the effective amount of said antibiotic is a concentration in the range which is non-lethal to the bacterium that causes the infection and causes 40% to 60% inhibition of the growth of said bacterium.

6. The method according to claim 1, wherein said self-replicating bacteriophage strain is at least one selected from the group consisting of *Cystoviridae, Leviviridae, Myoviridae, Podoviridae, Siphoviridae, Corticoviridae, Inoviridae, Microviridae*, and *Tectiviridae*.

7. The method according to claim 1, wherein said self-replicating bacteriophage strain is at least one selected from the group consisting of *Myoviridae, Podoviridae* and *Siphoviridae*.

8. The method according to claim 1, wherein said self-replicating bacteriophage strain is a *Myoviridae*.

9. The method according to claim 1, wherein the composition comprising at least one antibiotic, and the composition comprising at least one self-replicating bacteriophage are administrated intravenously, intranasally or orally to a mammal.

10. The method according to claim 1, wherein the effective amounts of self-replicating bacteriophage and antibiotic, in combination, enable killing or obliteration of sufficient bacterial microorganisms to render the microorganisms incapable of causing an infection of the host.

11. The method according to claim 1, wherein the composition comprising an effective amount of at least one self-replicating bacteriophage and the composition comprising an effective amount of antibiotic are administrated simultaneously to a mammal.

12. The method according to claim 1, wherein the composition comprising the effective amount of the at least one self-replicating bacteriophage is administrated to the mammal one day before or after the administration of the composition comprising the at least one antibiotic.

13. The method according to claim 1, wherein the composition comprising the effective amount of the at least one self-replicating bacteriophage is administrated to the mammal about 12 hours before or after the administration of the composition comprising the at least one antibiotic.

14. The method according to claim 1, wherein the composition comprising the effective amount of the at least one self-replicating bacteriophage is administrated to the mammal about 6 hours before or after the administration of the composition comprising the at least one antibiotic.

15. The method according to claim 1, wherein the composition comprising the effective amount of the at least one self-replicating bacteriophage is administrated to the mammal about 1 hour before or after the administration of the composition comprising the at least one antibiotic.

* * * * *